(12) United States Patent
Masini

(10) Patent No.: US 6,558,426 B1
(45) Date of Patent: May 6, 2003

(54) MULTIPLE-CAM, POSTERIOR-STABILIZED KNEE PROSTHESIS

(75) Inventor: Michael A. Masini, Ann Arbor, MI (US)

(73) Assignee: MedIdea, LLC, Ann Arbor, MI (US)

( * ) Notice: Subject to any disclaimer, the term of this patent is extended or adjusted under 35 U.S.C. 154(b) by 140 days.

(21) Appl. No.: 09/724,100

(22) Filed: Nov. 28, 2000

(51) Int. Cl.[7] ................................................. A61F 2/38
(52) U.S. Cl. .................................. 623/20.27; 623/20.14
(58) Field of Search .......................... 623/20.15, 20.16, 623/20.24, 20.25, 20.27, 20.28, 20.31, 20.33, 20.35

(56) References Cited

U.S. PATENT DOCUMENTS

| | | | |
|---|---|---|---|
| 4,650,490 A | 3/1987 | Figgie, III | 623/20 |
| 4,888,021 A | 12/1989 | Forte et al. | 623/20 |
| 4,892,547 A | 1/1990 | Brown | 623/20 |
| 4,936,847 A | 6/1990 | Manginelli | 623/23 |
| 4,936,853 A | 6/1990 | Fabian et al. | 623/20 |
| 4,959,071 A | 9/1990 | Brown et al. | 623/20 |
| 5,007,932 A | 4/1991 | Bekki et al. | 623/18 |
| 5,007,933 A | 4/1991 | Sidebotham et al. | 623/20 |
| 5,011,496 A | 4/1991 | Forte et al. | 623/20 |
| 5,133,759 A | 7/1992 | Turner | 623/20 |
| 5,147,405 A | 9/1992 | Van Zile et al. | 623/20 |
| 5,147,406 A | 9/1992 | Houston et al. | 623/20 |
| 5,152,797 A | 10/1992 | Luckman et al. | 623/20 |
| 5,236,461 A | 8/1993 | Forte | 623/20 |
| 5,330,532 A | 7/1994 | Ranawat | 623/20 |
| 5,330,534 A | 7/1994 | Herrington et al. | 623/20 |
| 5,358,527 A | 10/1994 | Forte | 623/20 |
| 5,370,699 A | 12/1994 | Hood et al. | 623/20 |
| 5,480,445 A | 1/1996 | Burkinshaw | 623/20 |
| 5,549,686 A | 8/1996 | Johnson et al. | 623/20 |
| 5,549,687 A | 8/1996 | Coates et al. | 623/20 |
| D374,078 S | 9/1996 | Johnson et al. | D24/155 |
| 5,554,158 A | 9/1996 | Vinciguerra et al. | 606/80 |
| 5,639,279 A | 6/1997 | Burkinshaw et al. | 623/20 |
| 5,658,342 A | 8/1997 | Draganich et al. | 623/20 |
| 5,702,458 A | 12/1997 | Burstein et al. | 623/20 |
| 5,800,552 A | 9/1998 | Forte | 623/20 |
| 5,824,100 A | 10/1998 | Kester et al. | 623/20 |
| 5,879,392 A | 3/1999 | McMinn | 623/20 |
| 5,997,577 A | 12/1999 | Herrington et al. | 623/20 |

*Primary Examiner*—David J. Isabella
*Assistant Examiner*—Kamrin Landrem
(74) *Attorney, Agent, or Firm*—Gifford, Krass, Groh, Sprinkle, Anderson & Citkowski, PC

(57) ABSTRACT

A distal femoral knee-replacement component provides additional points of cam action to facilitate a more normal rollback while inhibiting initial translation which could lead to increased wear and sub-optimal patella femoral mechanics. The inventive component preferably includes additional points of cam action, useable separately or together, to prevent early translation at the initiation of flexion, and a distinct point of cam action to prevent a dislocation of the femoral component over the tibial post which often occurs in cruciate-substituting designs. The preferred embodiment includes three distinct point of cam action. The first is preferably located substantially where existing cams are found, namely, at a point spaced apart a slight distance posteriorly relative to the post in full extension. A second point of cam action is located immediately adjacent the posterior aspect of the superior post to minimize and, ideally, prevent anterior translation at the initiation of flexion. The third point of cam action is preferably located more posteriorly to allow enhanced flexion without a dislocation of the cams over the post. The points of cam action may be implemented using any member or combination of elements operative to provide distinct stages of cooperation with the posterior aspect of the superior post. For example, transverse bars may be used which bridge, or partially bridge, the intercondylar space. The members or elements need not be straight across, but may instead be curved, with the post being curved to allows for a rotation, if so desired. The cam structures according to the invention may also be connected to one another forming points of contact as opposed to complete transverse elements such as distinct bars.

16 Claims, 4 Drawing Sheets

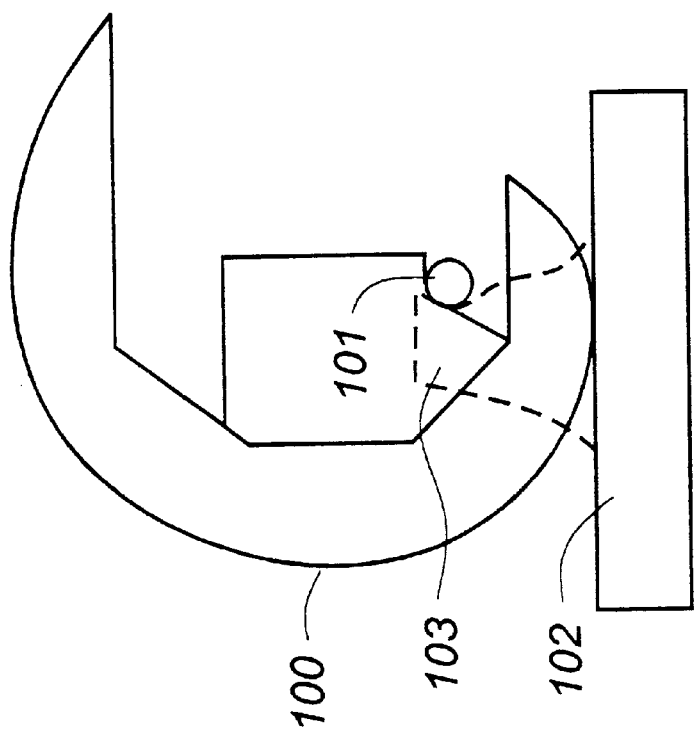
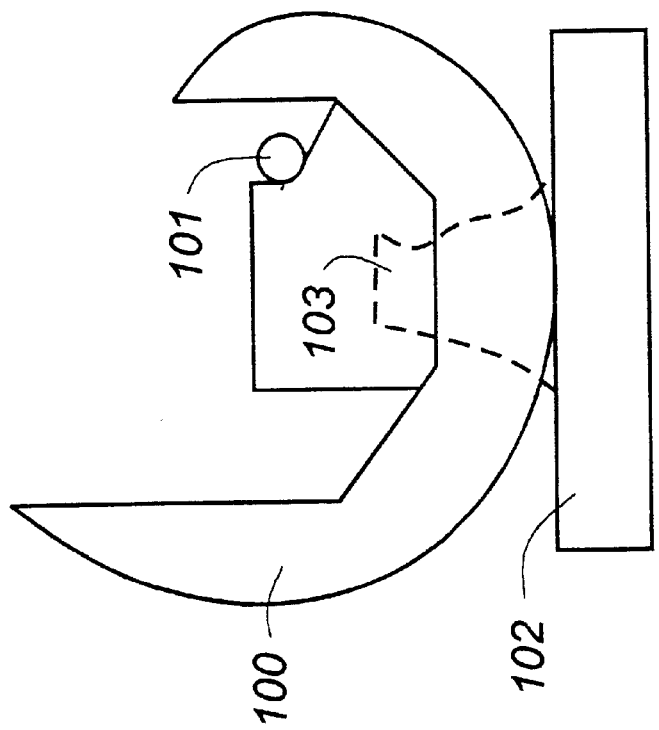

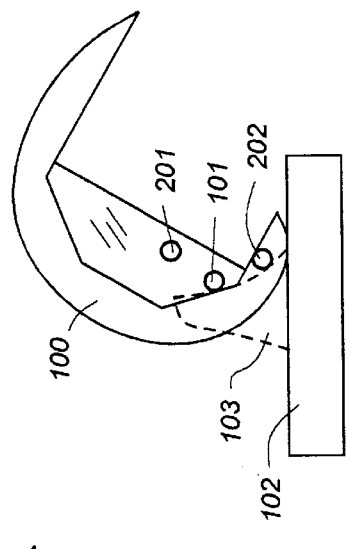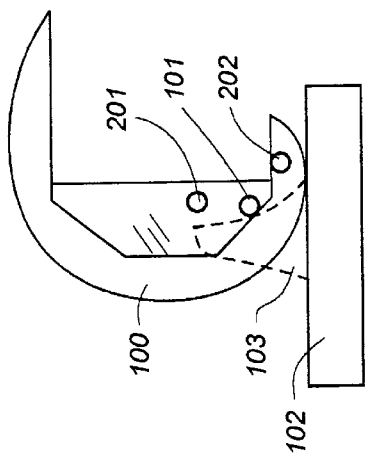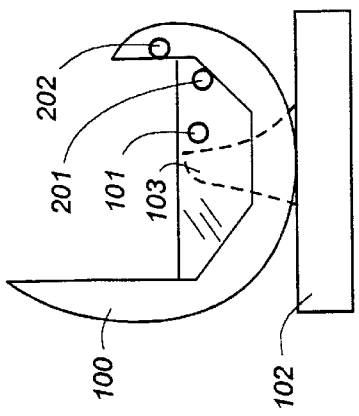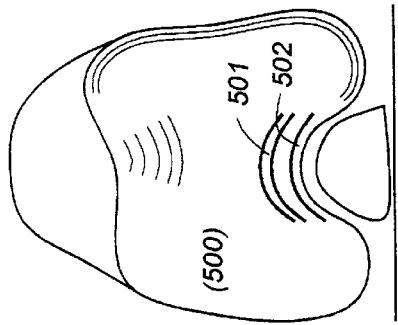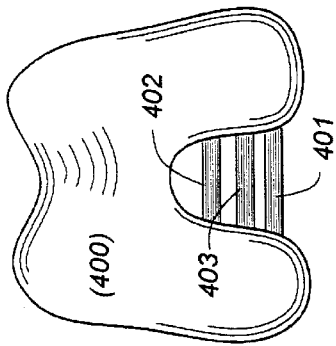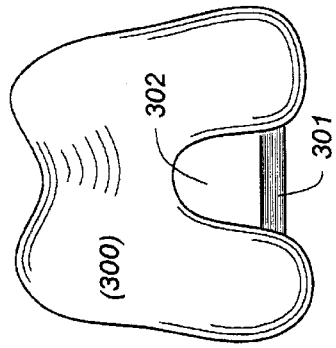

MULTIPLE-CAM, POSTERIOR-STABILIZED KNEE PROSTHESIS

FIELD OF THE INVENTION

This invention relates generally to orthopedic surgery and, in particular, to a posterior stabilized knee prosthesis.

BACKGROUND OF THE INVENTION

In total knee-replacement (TKR) surgery, there are four broad classes of implants used for resurfacing of the distal femur. In one configuration, the posterior cruciate ligament is retained. In another design the ligament is sacrificed, relying on the articular geometry to provide stability. The third type of device is constrained, in the sense that an actual linkage is used between the femoral and tibial components. According to a fourth arrangement, the posterior cruciate is replaced with a cam on the femoral component and a post on the tibial component.

Many patents have been issued in relation to these design configurations, including the cam-and-post design configuration. Some of the earlier patents in this area include U.S. Pat. No. 4,213,209 to Insall et al; U.S. Pat. No. 4,298,992 to Burstein et al.

Other patents include U.S. Pat. No. 4,888,021 to Forte et al., which teaches a cam-and-post mechanism as well as a linking mechanism. Essentially, each component includes a varying surface and a cam member, so that both the tibial and the femoral component have separate and distinct cams that cooperate with a single tibial post.

U.S. Pat. No. 5,824,100 to Kester et al. discloses a cam/post type of arrangement with a unique type of cam and box enclosure. A portion of the box enclosure is intended to prevent hyperextension and posterior translation. As noted in particular in FIGS. 3 and 4 of the '100 patent, a large space exists between the cam 110 and the post 100 which permits a translation to occur prior to engagement of the cam left of post.

U.S. Pat. No. 5,997,577 to Herrington et al. provides a cam on the femur with a geometry meant to contact the post through a large range of motion. This design attempts to provide the function of multiple cams by providing an area that acts as a separate bearing surface. As such, the cam effectively moves through a range of motion while contacting the post. Depending on the articular geometry which differs than the geometry of the cam post mechanism, this could lead to a variety of problems as well as significantly constrained motion, either between the cam and the post or between the two articulating surfaces.

U.S. Pat. No. 5,658,342 to Draganich et al. describes a cam member with including a bearing surface at complimenting an articulating surface. As in other previous designs, this represents a complex cam geometry meant to capture the post in certain degrees of the range of motion.

U.S. Pat. No. 5,147,405 to Van Zyle et al. Discloses a femoral component with two distinct cam structures, one located at point 44, the other located at 46 in the drawings. The cam member 44 is meant to contact the anterior surface of the post 24 to prevent hyperextension, while cam surface 46 is a posterior located cam meant to have contact throughout the range of flexion. As noted in FIG. 6A of the '405 patent, there is a space between the cam and the post when the knee is in extension, necessitating anterior translation of the femur on the tibia prior to contacting the posterior cam.

Many other patents directed to knee-replacement surgery include cam-and-post mechanisms. But in all cases, either the full range of joint motion is precluded, or translation is allowed to occur which could lead to premature wear. FIG. 1 is a drawing which illustrates a typical prior-art cam-and-post mechanism. Item 102 is a tibial insert or tibial component having a post 103 protruding into a box-like recess of the femoral component 100. FIG. 1A shows the system in extension, whereas FIG. 1B shows the system in flexion. In FIG. 1A, a femoral component 100 includes a cam 101 which has not yet engaged with a post 103.

In FIG. 1B, following a considerable amount of flexion, the cam 101 finally engages with the post 103. Until engagement occurs, however, the component 100 may be permitted to slide relative to the tibial insert. The need remains, therefore, for an improved distal femoral prosthesis having multiple distinct cams contacting a post on its posterior surface to a provide more normal range of motion for cruciate substituting knee replacement.

SUMMARY OF THE INVENTION

The present invention resides in a distal femoral knee-replacement component configured for use in a cruciate-substituting situation involving a tibial component having a bearing surface and a superior post with a posterior aspect. As with existing configurations, the component is comprised of a body having a pair of medial and lateral condylar protrusions and an intercondylar region therebetween dimensioned to receive the tibial post. In contrast to prior-art devices, however, the inventive component provides additional points of cam action to facilitate a more normal range of knee motion.

In the preferred embodiment, the invention facilitates a more normal rollback while inhibiting initial translation which could lead to increased wear and sub-optimal patella femoral mechanics. To accomplish this goal, the inventive component includes a distinct point of cam action to prevent early translation at the initiation of flexion, and a distinct point of cam action to prevent a dislocation of the femoral component over the tibial post which is known to occur in cruciate-substituting designs. According to the invention, these points of cam action may be used separately or in combination.

In the preferred embodiment, the component includes three distinct points of cam action. The first is preferably located substantially where existing cams are found, namely, at a point spaced apart a slight distance posteriorly relative to the post in full extension. According to the invention, however, a second point of cam action is located immediately adjacent the posterior aspect of the superior post to minimize and, ideally, prevent anterior translation at the initiation of flexion. The third point of cam action is preferably located more posteriorly to allow enhanced flexion without a dislocation of the knee.

In terms of structure, the points of cam action may be implemented using any member or combination of elements operative to provide distinct stages of cooperation with the posterior aspect of the superior post. For example, transverse bars may be used which bridge, or partially bridge, the intercondylar space. The members or elements need not be straight across, but may instead be curved, with the post being curved to allows for a rotation, if so desired. The cam structures according to the invention may also be connected to one another forming points of contact as opposed to complete transverse elements such as distinct bars.

BRIEF DESCRIPTION OF THE DRAWINGS

FIG. 1A is a drawing which illustrates a prior-art cam-and-post mechanism in extension;

FIG. 1B is a drawing which illustrates the prior-art cam-and-post mechanism of FIG. 1B in flexion;

FIG. 2A illustrates a preferred embodiment of the invention in extension;

FIG. 2B shows the system of FIG. 2A at 90 degrees flexion;

FIG. 2C illustrates the system of FIG. 2A in flexion at 120 degrees or more;

FIG. 3 shows an anterior view of a prior-art cruciate-substituting knee-replacement component;

FIG. 4 shows a knee prosthesis according to the invention having multiple cams as seen in a distal-to-proximal view;

FIG. 5 is a drawing which shows how cam-acting members according to the invention need not be straight across, but may be curved in conjunction with a curved post to facilitate rotation.

DETAILED DESCRIPTION OF THE INVENTION

FIGS. 2A through 2C illustrate one embodiment of the invention. FIG. 2A shows the configuration in extension, FIG. 2B shows the system at 90 degrees flexion, and FIG. 2C illustrates flexion of 120 degrees or more. In addition to a conventionally placed cam at 101, two additional points of cam action are preferably provided. In particular, a feature at 201 acts to prevent translation from extension into the initiation of the flexion. Feature 201 preferably disengages as conventional cam 101 is engaged. As the knee follows through a range of motion to 90° of flexion, and beyond, cam 101 disengages and feature 202 engages, if necessary, to prevent dislocation of the component.

Figure 2D:
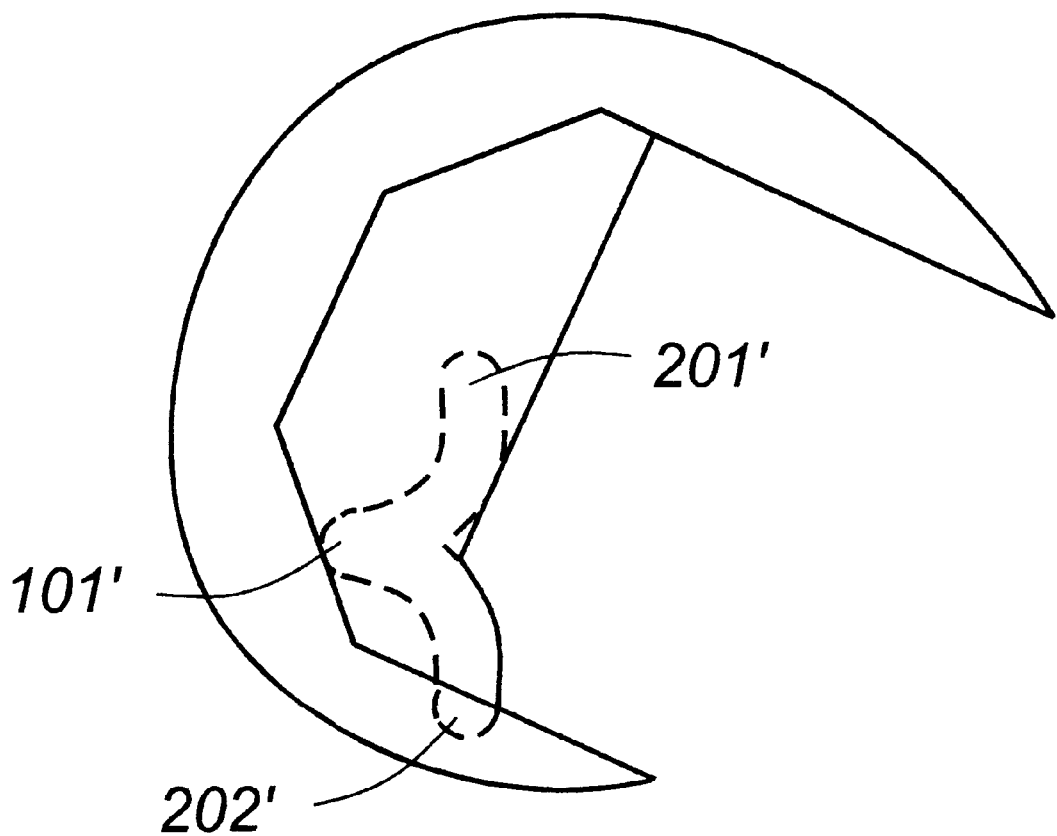
FIG. 2D illustrates the alternative use of interconnected cams with physically separate contact points.

In FIG. 2B, the cam which is usually present at 101 is engaging the tibial post, cam 201 has disengaged, and cam 202 has not yet engaged but is available for engagement on further flexion. In FIG. 2C, cam 202 is now engaged the post in the presence of additional flexion. Cam 101 can now disengage, cam 201 had disengaged earlier. FIG. 2D illustrates the alternative use of interconnected cams with physically separate contact points.

In FIGS. 2A through 4, the features depicted to provide the various stages of cam/pivoting function are depicted as bars which cross the intercondylar recess or box portion of a cruciate substituting design knee. However, although the terms "cam" or "bar" are used to reference the stages of cam action, it should be understood that the responsible structures may be implemented using any member or combination of elements operative to provide distinct stages of cooperation with the posterior aspect of the superior post. Thus, the members or elements need not be complete or straight across, but may instead be curved, with the post being curved to allows for a rotation, if so desired. The cam structures according to the invention may also be connected to one another forming points of contact as opposed to complete transverse elements. The structure may be provided as part of an open- or closed-type of a box structure, both being familiar to those of skill in the art.

Whereas FIGS. 1 and 2 represent lateral or side views of a knee through various ranges of motion, FIG. 3 shows an anterior view of a prior-art cruciate substituting knee component at 300 having an open-type box 302 including a single transverse member 301 for illustrative purposes. FIG. 4 shows a knee prosthesis 400 according to the invention, viewed again from the distal-to-proximal perspective, having three distinct points of cam action. In particular, cam 401 is conventionally located, an anterior cam is disposed at 402 in support of a greater range of enhanced flexion, and a more posterior cam at 403 is used primarily to prevent dislocation of the cams over the post, as discussed above.

FIG. 5 is a drawing which shows various cams from a top view looking down. Note that bars of need not be straight across, but may be curved with the post being curved so that it allows for a rotation to occur if desired. The cam structures according to the invention may be individual distinct bars or may be connected to one another forming points of contact as opposed to distinct structures themselves. It should also be noted that the cam structures may be located at different locations from the posterior to the anterior aspect of the knee design, as well as from the distal or proximal, depending upon implant size, patient physiology, desired range of motion, and other requirements. It should further be noted that as opposed to using three separate cams, one could use two cams intended to contact the posterior aspect of the post or for that matter, use more than three if desired.

Figure 6A:
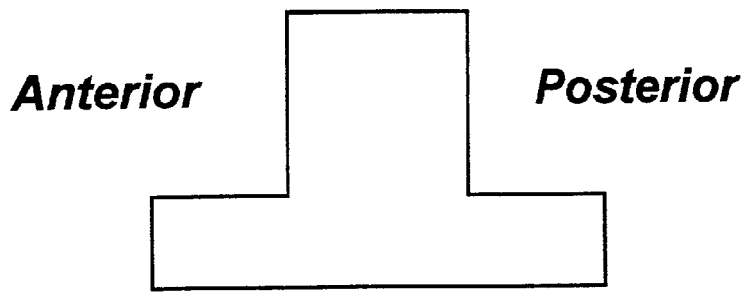
FIGS. 6A through 6E illustrate various alternative post configurations, all of which are applicable to the invention.
Figure 6B:
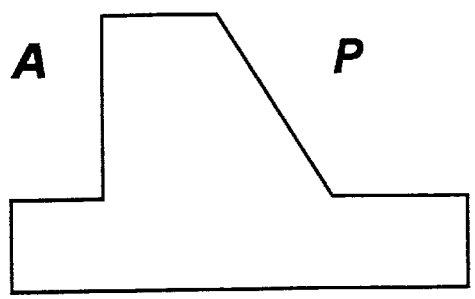
Figure 6C:
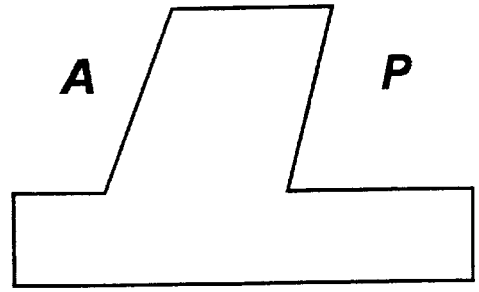
Figure 6D:
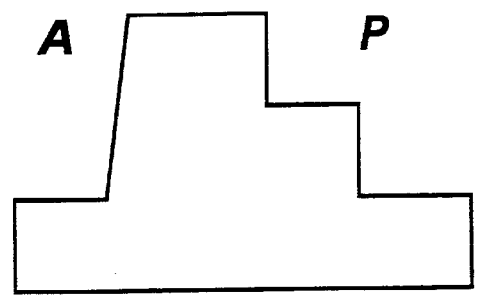
Figure 6E:
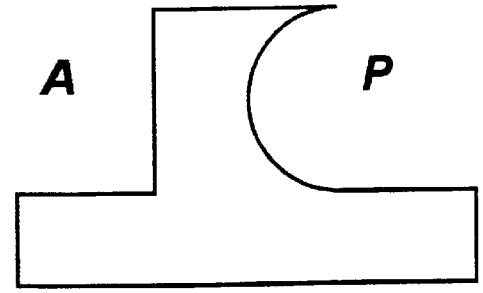

It will also be apparent to one of skill in the art that the posterior aspect of the post may be modified to affect the timing and/or operation of the cam engagement. FIGS. 6A through 6E illustrate various alternative post configurations, all of which are applicable to the invention. As opposed to a substantially straight configuration, as depicted in FIG. 6A, the post may be posteriorly oriented along the posterior aspect, as shown in FIG. 6B. Alternatively, the post may be anteriorly oriented along the posterior aspect, as shown in FIG. 6C. As further alternatives, the post may be stepped, as shown in FIG. 6D, or curved, as shown in FIG. 6E. Also, as opposed to the sharp corners shown, they may be rounded off, and the bars or recesses may be adjusted from the positions shown in FIGS. 2 through 5 to achieve a desired operation.

I claim:

1. A distal femoral knee-replacement component configured for use with a tibial component having a bearing surface and superior tibial post with a posterior aspect, the distal femoral component comprising:

a body having a pair of medial and lateral condylar protrusions and an intercondylar region therebetween dimensioned to receive the tibial post; and a plurality of members cam at least partially bridging the intercondylar region, the placement of the members being such that at all times one of the members engages with the posterior aspect of the tibial post through a range of motion from extension to flexion.

2. The distal femoral component of claim 1, wherein the members are spaced apart, generally parallel transverse bars that span the intercondylar region.

3. The distal femoral component of claim 2, wherein the bars are straight or curved.

4. The distal femoral component of claim 2, wherein the bars are interconnected but provide physically distinct contact points.

5. The distal femoral component of claim 2, wherein the post is concave and the bars are concave to permit rotation.

6. The distal femoral component of claim 1, including one cam member that engages with the posterior aspect of the tibial post at full extension to prevent translation of the condylar protrusions relative to the bearing surface at the initiation of flexion.

7. The distal femoral component of claim 1, including one cam member that engages with the posterior aspect of the tibial post to prevent dislocation in flexion beyond 90°.

8. The distal femoral component of claim 1, wherein the post features a posterior aspect which is slanted posteriorly.

9. A distal femoral knee-replacement component configured for use with a tibial component having a bearing surface and superior tibial post with a posterior aspect, the distal femoral component comprising:
 a body having a pair of medial and lateral condylar protrusions and an intercondylar region therebetween dimensioned to receive the tibial post; and
 a structure providing more than one physically separate and discontinuous points of cam action as the knee moves from extension to flexion.

10. The distal femoral component of claim 9, whereby the cam member of cam action is operative to minimize translation of the condylar protrusions relative to the bearing surface of the tibial component at the initiation of flexion.

11. The distal femoral component of claim 9, whereby the cam member of cam action is operative to minimize dislocation of the joint at a degree of flexion beyond 90 degrees.

12. The distal femoral component of claim 9, wherein the points of cam action are implemented as features which at least partially bridge the intercondylar region.

13. The distal femoral component of claim 12, wherein the features are transverse bars that span the intercondylar region.

14. The distal femoral component of claim 12, wherein the bars are straight or curved.

15. The distal femoral component of claim 12, wherein the post is convex and the bars are concave to permit rotation.

16. The distal femoral component of claim 9, wherein the post features a posterior aspect which is slanted posteriorly.

* * * * *